US012779093B2

(12) United States Patent
Kim et al.

(10) Patent No.: US 12,779,093 B2
(45) Date of Patent: Nov. 3, 2026

(54) 3D HYDROGEL COMPOSITE HAVING CANCER CELL APOPTOTIC EFFECT AND PREPARATION METHOD THEREOF

(71) Applicant: DONGGUK UNIVERSITY INDUSTRY-ACADEMIC COOPERATION FOUNDATION, Seoul (KR)

(72) Inventors: Kyo Bum Kim, Seoul (KR); Wonjeong Lee, Pohang-si (KR); Sung Jun Kim, Seoul (KR)

(73) Assignee: DONGGUK UNIVERSITY INDUSTRY-ACADEMIC COOPERATION FOUNDATION, Seoul (KR)

( * ) Notice: Subject to any disclaimer, the term of this patent is extended or adjusted under 35 U.S.C. 154(b) by 199 days.

(21) Appl. No.: 18/914,283

(22) Filed: Oct. 14, 2024

(65) Prior Publication Data

US 2025/0032676 A1 Jan. 30, 2025

Related U.S. Application Data

(63) Continuation of application No. PCT/KR2023/005249, filed on Apr. 18, 2023.

(30) Foreign Application Priority Data

Apr. 20, 2022 (KR) ........................ 10-2022-0048977
Apr. 18, 2023 (KR) ........................ 10-2023-0050905

(51) Int. Cl.

*A61L 27/52* (2006.01)
*A61L 27/04* (2006.01)
*A61L 27/18* (2006.01)
*A61L 27/22* (2006.01)
*A61L 27/54* (2006.01)

(52) U.S. Cl.

CPC ............... *A61L 27/52* (2013.01); *A61L 27/04* (2013.01); *A61L 27/18* (2013.01); *A61L 27/222* (2013.01); *A61L 27/54* (2013.01)

(58) Field of Classification Search

None
See application file for complete search history.

(56) References Cited

FOREIGN PATENT DOCUMENTS

| | | | |
|---|---|---|---|
| CN | 111514096 | A | 8/2020 |
| KR | 10-2015-0043241 | A | 4/2015 |
| KR | 10-2016-0110740 | A | 9/2016 |
| KR | 10-2021-0072741 | A | 6/2021 |
| KR | 10-2021-0107029 | A | 8/2021 |

OTHER PUBLICATIONS

Ji Hee Kange et al., Lipid-coated gold nanocomposites for enhanced cancer therapy, 2015, vol. 10, pp. 33-45. (Year: 2015).*

* cited by examiner

*Primary Examiner* — Nannette Holloman
(74) *Attorney, Agent, or Firm* — NKL LAW; Jae Youn Kim

(57) ABSTRACT

The present invention relates to the three-dimensional hydrogel composite with cancer cell targeting and apoptotic effects, and its preparing method. Specifically, it involves the three-dimensional hydrogel composite containing liquid metal particles that induce photothermal reactions upon near-infrared irradiation, along with chemically bonded anti-cancer agents for immobilization, and its preparing method. The three-dimensional hydrogel composite of the present invention is suitable for combination therapy involving photothermal treatment and chemotherapy. Therefore, it can be effectively utilized as a nano carrier for the treatment of various cancer cell types, contributing to a wide range of medical applications for effective cancer treatment.

14 Claims, 11 Drawing Sheets

3D HYDROGEL COMPOSITE HAVING CANCER CELL APOPTOTIC EFFECT AND PREPARATION METHOD THEREOF

CROSS-REFERENCES TO RELATED APPLICATIONS

This application is a continuation of co-pending International Application No. PCT/KR2023/005249, filed on Apr. 18, 2023, which is incorporated herein by reference in its entirety, and additionally claims priority from Korean Application No. KR 10-2022-0048977, filed on Apr. 20, 2022, and Korean Application No. KR 10-2023-0050905, filed on Apr. 18, 2023, which is incorporated herein by reference in its entirety.

TECHNICAL FIELD

The present invention relates to the three-dimensional hydrogel composite having a cancer cell apoptotic effect, and a preparation method thereof, and more specifically, to the three-dimensional hydrogel composite having a physical property which is injectable into cancer tissue, the composite comprises liquid metal particles for causing a photothermal reaction by near infrared rays and an anticancer agent which can be released into cancer tissue, and a preparation method thereof.

BACKGROUND ART

Chemotherapy is still the main approach for cancer treatment and shows high efficacy even with small number of drugs. However, unintended consequences of nonspecific administration of free drugs, and discomfort s of patient limit various application of chemotherapy. Moreover, the difficulty of maintaining appropriate concentration of a drug in an effective therapeutic range over a certain period is another challenge for the direct use of the drug in chemotherapy.

Meanwhile, a purpose of a Drug Delivery System (DDS) is to deliver drugs to a treatment target for treating diseases including cancer, and as such a drug delivery system, nano carriers for rapidly and accurately delivering drugs without drug loss and side effects are drawing attention.

Nano carriers have good biocompatibility, are easily functionalized, rapidly absorbed into cells, have a large drug loading capacity, and are easier to prepare. Since most anticancer drugs are insoluble in water because of its hydrophobicity and influence a wide range of toxicity and normal cells when administered in the human body, side effects could be occurred. As described above, therefore, when nanocarriers which having excellent biocompatibility were used, more efficient drug delivery might be possible, but since the nanocarriers are merely passive delivery by the EPR effect (Enhanced permeability and retention effect), the therapeutic effect is limited. To overcome these disadvantages, an active targeting technique for inducing cancer tissues by introducing cancer cell-specific antibodies, peptides, or low molecular weight materials into drug delivery nanoparticles is in the spotlight. However, drug efflux occurs inside the nanoparticles before reaching the cancer cell, which can cause extensive toxicity and side effects. To this end, a technology in which drug release occurs only by external stimuli (temperature, light, pH, redox, enzyme, protein, etc.) to reduce side effects of drugs and increase treatment effects is being developed.

Meanwhile, a next-generation drug delivery system for treating cancer cells using target-oriented nanoparticles capable of drug-optical treatment has been developed, but it is still necessary to develop a technology for minimizing the loss of drugs and inducing drug release only at cancer cells. Accordingly, there has been an attempt to induce a photothermal effect through light irradiation in which various metal particles are injected into or around a cancer tissue and the metal particles may react to death of the cancer tissue and cancer cell, but the photothermal effect alone through single injection of the metal particles into the cancer tissue may not sufficiently induce death of the cancer tissue, and in the case of an injection agent in the form of a suspension containing the metal particles, there is a limitation in that the injection agent is dispersed around and outside a specific site resulting insufficient apoptotic effect. As described above, the current nano carrier system is basically administered with an anti-cancer agent and has limitations that can be used only as auxiliary means used in combination with the anti-cancer agent, and thus, development of the composite having an excellent cancer cell apoptotic effect is required by including both liquid metal particles and the anti-cancer agent to have a photothermal treatment effect and releasing the anti-cancer agent in a local region to minimize loss of the anti-cancer agent and induce release of the drug only in cancer cells, so that the composite can be injected and has a sufficient apoptotic effect even after injection.

DISCLOSURE

Technical Problems

An object of the present invention is to provide the three-dimensional hydrogel composite having an excellent cancer cell apoptotic effect.

Another object of the present invention is to provide a method for producing the three-dimensional hydrogel composite having excellent cancer cell apoptotic effect.

Another object of the present invention is to provide a pharmaceutical composition for preventing or treating cancer, containing the three-dimensional hydrogel composite.

Technical Solution

To solve the above problems, the present invention provides the three-dimensional hydrogel composite having an excellent cancer cell apoptotic effect.

In addition, the present invention provides a preparation method of the three-dimensional hydrogel composite having an excellent cancer cell apoptotic effect.

In addition, the present invention provides a pharmaceutical composition for preventing or treating cancer, containing the three-dimensional hydrogel composite.

Advantageous Effects

According to the present invention, the three-dimensional hydrogel composite of the present invention has a property of being injectable and contains both liquid metal particles which have a cancer cell apoptotic effect caused by photothermal reaction by means of near infrared rays, and an anticancer agent, which can be released into a cancer tissue, and can be used in a combination of photothermal therapy and chemotherapy. Therefore, the three-dimensional hydrogel composite of the present invention is an injection-type preparation for local cancer tissue treatment, containing gallium-indium liquid metal particles capable of inducing a photothermal effect for effective treatment of cancer and an anticancer agent capable of inducing cancer cell apoptosis, and thus can be widely used for the treatment of various cancer cells.

BRIEF DESCRIPTION OF DRAWINGS

In FIG. 3, the uppermost curve refers to a result obtained using 1,000 μg/mL, the intermediate curve refers to a result obtained using 100 μg/mL, and the lowermost curve refers to a result obtained using PBS.

In FIG. 5, the uppermost curve represents 10 mM GSH, and the lower curve represents Control (PBS).

In FIG. 7, the uppermost curve refers to a result obtained by using 1.5 $W/cm^2$, the upper-middle curve refers to a result obtained by using 1.0 $W/cm^2$, the lower-middle curve refers to a result obtained by using 0.5 $W/cm^2$, and the lowermost curve refers to a result obtained by using 1.5 $W/cm^2$ (w/o LLM).

In FIG. 8, the uppermost curve refers to the result of using 800 μg/mL, the upper-middle curve refers to the result of using 400 μg/mL, the lower-middle curve refers to the result of using 200 μg/mL, and the lower-lowest curve refers to the result of using 0 μg/mL.

In FIG. 10, the uppermost curve refers to a result of using LLM-6MP@hydrogel, the upper-middle curve refers to a result of using LLM-hydrogel, the lower-middle curve refers to a result of using Hydrogel, and the lower-lowest curve refers to a result of using control.

In FIG. 11, the curve located at the upper end means LLM-hydrogel, and the curve located at the lower end means LLM-hydrogel+Laser.

In FIG. 14, a curve rising to the top means LLM-hydrogel, and a curve located at the bottom means Hydrogel.

In FIG. 15, a curve rising to the top means LLM-6MP@hydrogel, and a curve located at the bottom means 6MP@hydrogel.

BEST MODE FOR INVENTION

Figure 1:
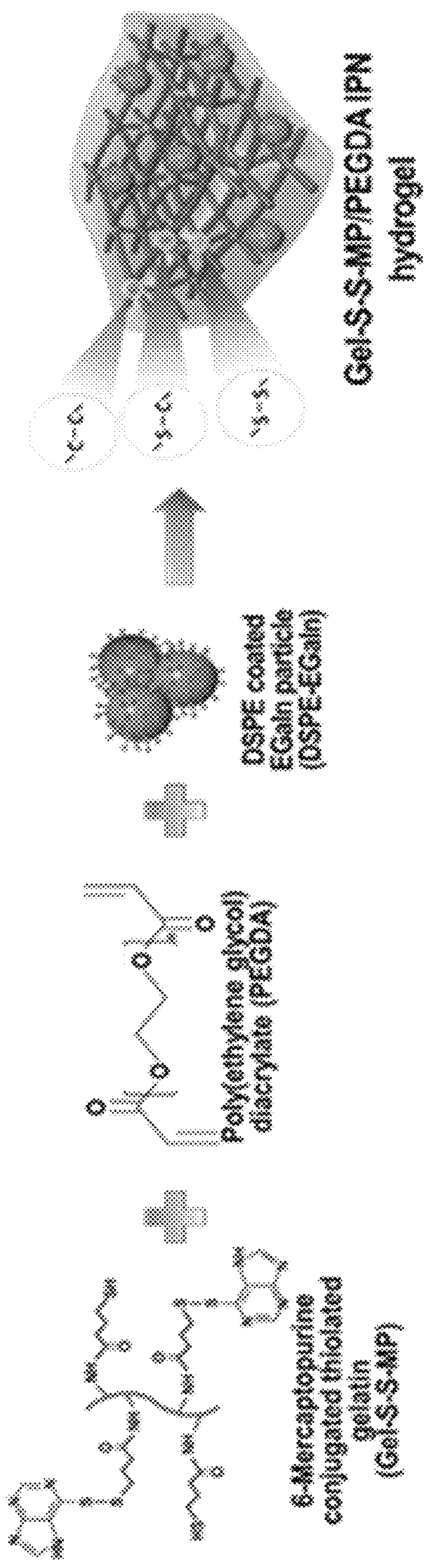
FIG. 1 is a diagram schematically showing the configuration of the three-dimensional hydrogel of the present invention using chemical formulas.

The present invention relates to the three-dimensional hydrogel composite having a cancer cell apoptotic effect, and a preparation method thereof, and more specifically, to the three-dimensional hydrogel composite having a physical property which is injectable into cancer tissue, the composite contains liquid metal particles for causing a photothermal reaction by near infrared rays; and an anticancer agent which can be released into cancer tissue, and a preparation method thereof.

MODE FOR INVENTION

The language used in the present specification and claims should not be construed as limited to ordinary or dictionary meanings, but should be construed as meaning and concept consistent with the technical idea of the invention based on the principle that the inventor can appropriately define the concept of the term in order to describe his or her invention in the best way. Therefore, since the configuration of the examples described in the present specification is only one most preferred embodiment of the present invention and does not represent all of the technical idea of the present invention, it should be understood that there may be various equivalents and modifications that can replace the examples at the time of filing the present application.

The terms used in the present invention have selected general terms that are currently widely used as possible while considering functions in the present invention, but may vary depending on the intention or precedent of a technician engaged in the art, the emergence of new technologies, etc. In addition, terms arbitrarily selected by the applicant may be used in specific cases, and in this case, the meaning thereof will be described in detail in the description of the corresponding invention. Therefore, the terms used in the present invention, should be defined based on the meanings of the terms and the contents throughout the present invention, rather than simple names of the terms.

Throughout the specification, when a part is described to "include" a certain component, this means that other components may be further included, rather than excluding other components, unless otherwise stated.

Specific embodiments are only illustrated and described in detail, and since the present invention can be variously changed and have various forms, the present invention is not limited to the illustrated specific embodiments. It should be understood that the present invention includes all modifications, equivalents, and alternatives falling within the spirit and scope of the present invention.

Hereinafter, preferred embodiments of the present invention will be described in detail.

The present invention provides the three-dimensional hydrogel composite having an excellent cancer cell apoptotic effect.

As an embodiment, the three-dimensional hydrogel composite of the present invention may include liquid metal particles and an anticancer agent, and may be the three-dimensional hydrogel composite of which physical properties are adjusted to physical properties that can be injected through other polymer materials.

The liquid metal particles included in the three-dimensional hydrogel have a photothermal reaction by near-infrared rays to have a cancer cell killing effect, and the anticancer agent is released to a cancer tissue to have a cancer cell killing effect, and thus the three-dimensional hydrogel composite containing the liquid metal particles and the anticancer agent can be used for a combination of the photothermal treatment and the chemotherapy. More specifically, cancer cells are killed due to a photothermal effect induced by near-infrared irradiation of liquid metal particles, and a cancer cell-containing substance such as glutathione which flows out from the killed cancer cells enhances the reducing condition in the microenvironment of cancer tissue, and induces the cleavage of a disulfide bond connecting a hydrogel with an anticancer agent due to the reducing condition formed as described above, such that the anticancer agent released by the cleavage of the disulfide bond under the above conditions induces additional killing of surrounding cancer cells, thereby enhancing the anticancer effect, and thus can be used for a combination of photothermal therapy and chemotherapy.

As an example, the liquid metal contained in the liquid metal particle may be any one or more selected from the group consisting of gold, platinum, silver, and gallium-indium, and more specifically, may be gallium-indium, but is not limited thereto.

In the present invention, the liquid metal particles may cause a photothermal reaction by near-infrared rays, and the photothermal therapy is a treatment method of treating cancer by absorbing energy from photons and partially using the energy in the form of heat, and is a treatment method of inducing cancer cell apoptosis by increasing the temperature when a multi-nano-sized agent is accumulated near a tumor. Due to heat rise caused by near-infrared irradiation, the anticancer agent may be released into cancer tissue, and localized therapeutic heat may change, remove, or destroy target tissue.

In addition, in the present invention, external optical stimulation including near-infrared ray provides localized heat from liquid metal particles in a target region, destroys tissue and cells for photothermal treatment, and the elevated temperature selectively promotes anticancer agent release through sensitization according to reductive environmental conditions in cancer cells/cancer tissues for chemotherapy.

As used herein, the term "drug" refers to a substance capable of inhibiting, inhibiting, reducing, alleviating, delaying, preventing, or treating diseases or symptoms in animals including humans, and a representative example thereof is an anticancer drug.

For example, the three-dimensional hydrogel composite of the present invention may further include and anticancer agent capable of being released into caner tissue through polymer materials and chemical bonding. Specifically, the anticancer agent with apoptotic effects on cancer cells within the cancer tissue may be selected from a group consisting of 6-mercaptopurine, paclitaxel, doxorubicin, 5-fluorouracil, cisplatin, carboplatin, oxaliplatin, tegafur, irinotecan, docetaxel, cyclophosphamide, cemcitabine, ifosfamide, mitomycin C, vincristine, etoposide, methotrexate, topotecan, tamoxifen, vinorelbine, camptothecin, danuorubicin, chlorambucil, bryostatin-1, calicheamicin, mayatansine, levamisole, DNA recombinant interferon alpha-2a, mitoxantrone, nimustin, interferon alpha-2a, doxifluridine, formestane, leuprolide acetate, megestrol acetate, carmofur, teniposide, bleomycin, carmustine, heptaplatin, exemestane, anastrozeole, estramustine, cepecitabine, goserelin acetate, polysaccharide potassuim, medroxypogesterone acetate, epirubicin, letrozole, pirarubicin, topotecan, altretamine, toremifenecitrate, BCNU, taxotere, actinomycin D, and gemcitabine, and more specifically, the anticancer agent may be 6-cmercaptopurine. The anticancer agent is chemically bounded to the polymer material, which can be gelatin as example, and is conjugated through cleavable chemical bond within the microenvironment of cancer cells and/or cancer tissue, allowing drug release based on the reducing conditions of cancer cells and/or cancer tissue. In this case, the chemical bonding may include disulfide bonds.

In the present invention, the liquid metal particles may be surface-modified to prevent aggregation of aqueous solution phase particles and increase long-term storage stability, and the surface-modifying material may be, for example, any one or more selected from the group consisting of lipid molecules including DSPC (1,2-distearoyl-sn-glycero-3-phosphocholine), DSPE (1,2-Distearoyl-sn-glycero-3-phosphoethanolamine), DOPE (1,2-Dioleoyl-sn-glycero-3-phosphoethanolamine), cholesterol, and the like, natural polymers including dextran, hyaluronic acid, and the like, and synthetic polymers including PEG (poly(ethylene glycol)), and more specifically, DSPE (1,2-Distearoyl-sn-glycero-3-phosphoethanolamine), but is not limited thereto.

For example, the surface-modified liquid metal particles can be prepared by using liquid metal and a surface-modified material through the following process, but are not limited thereto.

First, gallium-indium liquid metal and DSPE as a surface-modified material are dissolved and mixed in an organic solvent including chloroform, and then a liquid metal in the form of particles in which the surface-modifying material is modified on the surface is obtained in the solvent through an ultrasonic pulverization process. Thereafter, after removing the organic solvent through a drying process, the surface-modified liquid metal particles dispersed in distilled water are ultrasonically pulverized again to secure the surface-modified liquid metal particles as a final material.

In addition, for example, the anticancer agent may be coordinated to a polymer material through a chemical bond, and the process may be as follows, but is not limited thereto.

After solubilize polymer material in water, mix with EDTA (ethylene-diamine-tetraacetic acid) and imidazole, and then stir for 24 hours. Then, after reacting with β-mercaptoethanol to connect a thiol group to the polymer material, the anticancer agent dissolved in mixed solution of distilled water and dimethyl sulfoxide, and the polymer material to which the thiol group is connected are mixed, stirred for 24 hours, and freeze-dried to finally prepare a polymer material to which the anticancer agent is chemically bonded.

As an example, the bond connecting the anticancer agent and the polymer material is a chemical bond, and an example of such a chemical bond may include a disulfide bond, and the polymer material may be gelatin, but is not limited thereto.

Thereafter, the mixture in which the polymer material to which the anticancer agent is bound and the liquid metal particles having the modified surface are mixed may be mixed again with other polymer materials for adjusting physical properties through the following process to prepare the three-dimensional hydrogel composite. For example, the physical and/or mechanical properties of the three-dimensional hydrogel may be adjusted to enable injection, and in this case, the properties may be adjusted according to the mixing ratio of each material.

The preparing process of the three-dimensional hydrogel composite having the adjusted physical properties may be as follows, but is not limited thereto.

The three-dimensional hydrogel, which includes the polymer material bound to the anticancer agent and the liquid metal particles of the present invention, can be prepared as an injectable physical material by controlling its properties with other polymer materials. These other polymer materials may include poly(ethylene glycol) diacrylate, among others, and may also include an initiator that induces thermally reactive crosslinking. The initiator could be ammonium persulfate or tetramethylethylenediamine (TEMED), but is not limited to these examples.

Furthermore, the anticancer drug-bound polymer materials and the polymer materials used to control the hydrogel's properties should be soluble in solutions similar to water, cell culture solutions, or body fluids.

As an exemplary embodiment of the present invention, the three-dimensional hydrogel composite may be used simultaneously as a photoreactive reagent and a drug delivery vehicle. The cancer may be at least one selected from the group consisting of pseudomyxoma, intrahepatic biliary tract cancer, hepatoblastoma, liver cancer, thyroid cancer, colon cancer, testicular cancer, myelodysplastic syndrome, glioblastoma, oral cancer, lip cancer, mycosis fungoides, acute myeloid leukemia, acute lymphocytic leukemia, basal cell cancer, ovarian epithelial cancer, ovarian germ cell cancer, male breast cancer, brain cancer, pituitary adenoma, multiple myeloma, gallbladder cancer, biliary tract cancer, colorectal cancer, chronic myelogenous leukemia, chronic lymphocytic leukemia, retinoblastoma, choroid melanoma, diffuse-large B-cell lymphoma, ampulla of Vater cancer, bladder cancer, peritoneal cancer, nonfunctional parathyroid carcinoma, cancer of the adrenal gland, nasal sinus cancer, non-small cell lung cancer, non-Hodgkin lymphoma, tongue cancer, astrocytoma, small cell lung cancer, pediatric brain tumor, pediatric lymphoma, childhood leukemia, small intestine cancer, meningioma, esophageal cancer, glioma, neuroblastoma, renal pelvic cancer, renal cancer, heart cancer, duodenal cancer, malignant soft tissue cancer, malignant bone cancer, malignant lymphoma, malignant mesothelioma, malignant melanoma, eye cancer, vulvar cancer, ureteral cancer, urethral cancer, primary unspecified cancer, gastric lymphoma, gastric cancer, gastric carcinoma, gastrointestinal stromal tumor, Wilms tumor, breast cancer, sarcoma, penile cancer, pharyngeal cancer, choriocarcinoma of pregnancy, cervical cancer, endometrial cancer, uterine sarcoma, prostate cancer, metastatic bone cancer, metastatic brain cancer, mediastinal tumors, rectal cancer, colorectal carcinoma, vaginal cancer, spinal cancer, acoustic schwannoma, pancreatic cancer, salivary gland cancer, Kaposi's sarcoma, Paget's disease, tonsil cancer, squamous cell carcinoma, lung adenocarcinoma, lung cancer, lung squamous cell carcinoma, skin cancer, anal cancer, rhabdomyosarcoma, laryngeal cancer, pleural cancer, and thymic cancer.

In addition, the cancer is a solid tumor and may be any one or more selected from the group consisting of gastric cancer, liver cancer, glioblastoma, ovarian cancer, colorectal cancer, head and neck cancer, cervical cancer, bladder cancer, renal cell cancer, breast cancer, metastatic cancer, prostate cancer, pancreatic cancer, melanoma, esophageal cancer, colon cancer, hepatocellular cancer, and lung cancer. More specifically, it may be any one or more selected from the group consisting of breast cancer, colorectal cancer, and cervical cancer, but is not limited thereto.

In addition, as an embodiment of the present invention, the three-dimensional hydrogel composite with an immobilized active ingredient, such as a drug, may be used to provide photothermal therapy, chemotherapy, or a combination of both.

More specifically, the liquid metal particles included in the aforementioned the three-dimensional hydrogel induce a photohermal reaction upon exposure to near-infrared rays, resulting in an apoptotic effect on cancer cells. Additionally, since the anticancer agent is released into the cancer tissue, it also possesses and apoptotic effect on cancer cells. Therefore, the three-dimensional hydrogel composite containing the liquid metal particles and the anticancer agent can be used for the combination therapy of photothermal therapy and chemotherapy.

Specifically, upon near-infrared irradiation of the liquid metal particles, a photothermal effect is induced, leading to the apoptosis of cancer cells. Substances contained within the apoptotic cancer cells, such as glutathione, enhance the reducing conditions of the cancer tissue microenvironment. As a result, the cleavage of disulfide bonds connecting the hydrogel and the anticancer agent is induced under these reducing conditions. The anticancer agent released due to the cleavage of disulfide bonds further induces additional apoptosis of surrounding cancer cells, thereby enhancing the anticancer effect. Consequently, this approach can be used for combination therapy involving both photothermal therapy and chemotherapy.

The photothermal therapy and combination therapy method using an anticancer agent provide a synergistic effect by simultaneously delivering the anticancer agent. This approach minimizes systemic side effects and improves the cytotoxic effect by inducing localized heat at the targeted tumor site.

In a preferred embodiment of the present disclosure, the three-dimensional hydrogel composite may be prepared by the following process.

More specifically, the preparation method of the three-dimensional hydrogel composite comprises the steps of:

*69(a) preparing liquid metal particles with a modified surface;

(b) chemically bonding an anticancer agent;

(c) mixing the surface-modified liquid metal particles prepared in step (a) and the chemically bonded anticancer agent prepared in step (b) with other polymer materials to manufacture the three-dimensional hydrogel composite, with adjusted physical properties to allow for injection In the present invention, step (a) is the preparation of surface-modified liquid metal particles. More specifically, DSPE (1,2-Distearoyl-sn-glycero-3-phosphoethanolamine) as the surface-modifying material is dissolved and mixed in an organic solvent including chloroform. The surface-modified material is then obtained in the form of particles modified on the surface of the liquid metal through an ultrasonic pulverization process. After removing the organic solvent through a drying process, the method includes ultrasonically pulverizing the liquid metal particles with the modified surface dispersed in distilled water again to secure the final material.

For example, the surface-modified material may be one or more selected from the group consisting of lipid molecules, such as DSPC (1,2-Distearoyl-sn-glycero-3-phosphocholine), DSPE (1,2-Distearoyl-sn-glycero-3-phosphoethanolamine), DOPE (1,2-Dioleoyl-sn-glycero-3-phosphoethanolamine), and cholesterol; natural polymers, such as dextran and hyaluronic acid; and synthetic polymers, such as poly(ethylene glycol) (PEG). Specifically, DSPE (1,2-Distearoyl-sn-glycero-3-phosphoethanolamine) may be used, but it is not limited thereto.

In addition, in the present invention, step (b) involves immobilizing the anticancer agent through chemical bonding. The anticancer agent is immobilized with a polymer material via disulfide bonds, and the polymer material may be gelatin, but is not limited thereto.

First, gelatin as a polymer material is dissolved in water, mixed with ethylenediaminetetraacetic acid (EDTA) and imidazole, and stirred for 24 hours. The method then includes reacting β-mercaptoethanol to attach a thiol group to the polymer material. Next, the anticancer agent, dissolved in a mixed solution of distilled water and dimethyl sulfoxide, is mixed with the thiol group-modified polymer material for 24 hours. The final step involves lyophilization to prepare the polymer material with the chemically bonded anticancer agent. For example, the bond connecting the anticancer agent and the polymer material is a chemical bond, such as a disulfide bond.

In this case, the anticancer agent may be 6-mercaptopurine, and the polymer material may be gelatin, but the present invention is not limited thereto. The bond connecting the anticancer agent and the polymer material is a chemical bond, enabling controlled release of the drug upon light irradiation.

In addition, in the present invention, step (c) involves mixing the surface-modified liquid metal particles prepared in step (a) with the anticancer agent immobilized by the chemical bond in step (b) and other polymer materials to prepare a three-dimensional hydrogel composite with physical properties adjusted for injection. This step includes adjusting the physical properties using other polymer materials. The other polymer materials may include poly(ethylene glycol) diacrylate, but are not limited thereto, and may further include an initiator capable of inducing thermally reactive cross-linking. The initiator may be ammonium persulfate or tetramethylethylenediamine (TEMED), but is not limited to these examples. For example, the initiator may be activated at a temperature similar to a body temperature to induce new thermal crosslinking between the polymer materials, and may promote gelation of the polymer materials dispersed in the liquid phase to finally form the three-dimensional structure.

In addition, as an example, the mixing volume ratio of the polymer material to which the anticancer agent is bound and the liquid metal particles, the other polymer material for adjusting physical properties, and the initiator may be 50:49:1 and/or the mass ratio may be 25:100:3, and more specifically, the mixing volume ratio may include a polymer material to which 25 mg of the anticancer agent is bound per 1 mL of the three-dimensional hydrogel, the other polymer material for adjusting physical properties of 100 mg, the liquid metal particles in which 2 mg of APS, 1 mg of TEMED, and 400 μg of the surface are modified, but the present invention is not limited thereto.

In addition, the anticancer drug-binding polymer material and the polymer material used to control hydrogel properties should be soluble in solutions similar to water, cell culture solutions, or body fluids.

Furthermore, the present invention provides a pharmaceutical composition for preventing or treating cancer, comprising the three-dimensional hydrogel containing the anticancer agent described herein.

As an example, the three-dimensional hydrogel containing an anticancer agent in the present invention exhibits an excellent cancer cell-killing effect due to the increased temperature from the photothermal effect mediated by the liquid metal, followed by the subsequent release of the anticancer agent.

In one embodiment, the cancer may be at least one selected from the group consisting of pseudomyxoma, intrahepatic biliary tract cancer, hepatoblastoma, liver cancer, thyroid cancer, colon cancer, testicular cancer, myelodysplastic syndrome, glioblastoma, oral cancer, lip cancer, mycosis fungoides, acute myeloid leukemia, acute lymphocytic leukemia, basal cell cancer, ovarian epithelial cancer, ovarian germ cell cancer, male breast cancer, brain cancer, pituitary adenoma, multiple myeloma, gallbladder cancer, biliary tract cancer, colorectal cancer, chronic myelogenous leukemia, chronic lymphocytic leukemia, retinoblastoma, choroid melanoma, diffuse-large B-cell lymphoma, ampulla of Vater cancer bladder cancer, peritoneal cancer, Nonfunctional parathyroid carcinoma cancer of adrenal gland nasal sinus cancer, non-small cell lung cancer non-Hodgkin lymphomas tongue cancer, astrocytoma, small cell lung cancer, pediatric brain tumor, pediatric Lymphoma, childhood leukemia, small intestine cancer, meningioma, Esophageal cancer, glioma, neuroblastoma, renal pelvic cancer, Renal cancer, Heart cancer, Duodenal cancer, Malignant soft tissue cancer, Malignant bone cancer, malignant lymphoma, malignant mesothelioma, malignant melanoma, eye cancer, Vulvar cancer, Ureteral cancer, Urethral cancer, Primary unspecified cancer, Gastric lymphoma, Gastric cancer, Gastric carcinoma, Gastrointestinal interstitial cancer, Wilms cancer, breast cancer, Sarcoma, Penile cancer, Pharyngeal cancer, Pregnancy choriosis, Cervical cancer, Endometrial cancer, Uterine sarcoma Prostate cancer, Metastatic bone cancer, Metastatic brain cancer, Mediastinal rocks, Rectal cancer, Colorectal carcinoma, Vaginal cancer, Spinal cancer, Auditory schwannoma, Pancreatic cancer, salivary gland cancer, Kaposi's sarcoma, Paget's disease, Tonsil cancer, squamous cell carcinoma, Lung adenocarcinoma, Lung cancer, lung squamous cell carcinoma, Skin cancer, Anal cancer, Rhabdomyosarcoma, laryngeal cancer, Pleural cancer, and thymic cancer, and more specifically, the solid tumor is more specifically breast cancer or colorectal cancer, but is not limited thereto.

In the present invention, the term 'prevention' refers to all actions that inhibit a disease, such as cancer, or delay its onset by administering the composition according to the present invention.

The term 'treatment' refers to all actions that improve or beneficially change the symptoms of cancer or similar diseases through the administration of the composition according to the present invention.

In the present invention, the 'pharmaceutical composition' may be in the form of capsules, tablets, granules, injections, ointments, powders, or beverages. The composition can be used in oral formulations such as powders, granules, capsules, tablets, aqueous suspensions, etc.; external preparations; suppositories; or sterile injectable solutions, but is not limited to these forms. The pharmaceutical composition may include a pharmaceutically acceptable carrier. For oral administration, the carrier may include binders, lubricants, disintegrants, excipients, solubilizers, dispersants, stabilizers, suspending agents, pigments, and fragrances. For injections, buffers, preservatives, analgesic agents, solubilizers, isotonic agents, and stabilizers may be used. For topical administration, bases, excipients, lubricants, and preservatives may be used.

The formulation of the pharmaceutical composition can be prepared in various ways by mixing with the pharmaceutically acceptable carrier. For example, the composition can be prepared in the form of tablets, troches, capsules, elixirs, suspensions, syrups, or wafers for oral administration, and as unit dose ampoules or multiple doses for injection. It can also be formulated into solutions, suspensions, tablets, capsules, or sustained-release preparations. Examples of suitable carriers, excipients, and diluents for formulation include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinylpyrrolidone, water, methylhydroxybenzoate, propylhydroxybenzoate, talc, magnesium stearate, and mineral oil. Additionally, fillers, anti-coagulants, lubricants, wetting agents, fragrances, emulsifiers, and preservatives may be included. Routes of administration of the pharmaceutical composition include, but are not limited to, oral, intravenous, intramuscular, intraarterial, intramedullary, intrathecal, intracardiac, transdermal, subcutaneous, intraperitoneal, intranasal, intestinal, topical, sublingual, or rectal. However, parenteral administration is preferred. The term 'parenteral' includes subcutaneous, intradermal, intravenous, intramuscular, intra-articular, intraspinal, intrathecal, intratracheal, and intracranial injection or infusion techniques. The dosage and administration of the pharmaceutical composition may vary based on factors including activity, age, body weight, general health, gender, injection or infusion time, injection or infusion route, discharge rate, drug combination, and the severity of the specific disease to be prevented or treated. The amount may also vary according to the condition, weight, severity of the disease, drug form, and administration route and period of the specific compound used. Appropriate dosages and administration methods can be determined by those skilled in the art.

Hereinafter, preferred examples are presented to aid in understanding the present invention. However, these examples are provided solely for the purpose of better understanding the invention and should not be construed as limiting its scope.

Example 1. Preparation of Liquid Metal Particles with a Modified Surface

Liquid metal particles with a surface-modified required for the preparation of the three-dimensional hydrogel of the present invention were prepared as following.

*93 First, 5.6 mg of the surface-modifying lipid molecule DSPE (1,2-Distearoyl-sn-glycero-3-phosphoethanolamine) was dissolved in 960 μL of chloroform, and then 20 mg of gallium-indium liquid metal ((eutectic Ga—In alloy (EGaIn), Sigma-Aldrich) (=3.2 μL) was added to DSPE/chloroform solution. Thereafter, the Ga—In liquid metal particles were generated in the solution through the bath sonication process twice at 50° C. for 20 minutes each, and then the solution was put in a dry air dryer for 24 hours or more to remove chloroform. Thereafter, the dried particles were dissolved in 12.8 mL of distilled water, subjected to sonication at 50° C. for 10 minutes, and then subjected to sonication using a probe sonicator to prepare a surface-modified liquid metal with a concentration of 2 mg/mL (Amplitude: 26%, Pulse: 5 s on/5 s off, time: 20 minutes).

Example 2. Combination of an Anticancer Drug and a Polymer Material Through a Chemical Bond An immobilized anticancer drug required for the preparation of the three-dimensional hydrogel was prepared by the following method.

First, gelatin as a polymer material was dissolved in water, mixed with ethylene-diamine-tetraacetic acid (EDTA) and imidazole, and then stirred for 24 hours to prepare a polymer material mixture. Thereafter, the polymer material mixture was reacted with β-mercaptoethanol to introduce thiol group to the polymer material, and then the anticancer agent dissolved in a mixed solution of distilled water and dimethyl sulfoxide and the polymer material to which the thiol group is connected were mixed and stirred for 24 hours, and freeze-dried to finally prepare a polymer material in which the anticancer agent is chemically bonded through a disulfide bond. In this case, 6-mercaptopurine was used as an anticancer agent.

Example 3. Preparation of the Three-Dimensional Hydrogel Composite of which Physical Properties are Adjusted to Enable Injection The three-dimensional hydrogel composite of which physical properties were adjusted through other polymer materials using the liquid metal particles of which the surface was modified in Example 1 and the polymer material to which the anticancer agent prepared in Example 2 was bound was prepared in the following process.

Poly(ethylene glycol) diacrylate was used as a polymer material to adjust physical properties, and ammonium persulfate and tetramethylenediamine (TEMED) were added and mixed as initiators capable of inducing thermally reactive cross-linking, and in this case, a polymer material in which 25 mg of an anticancer agent was combined per 1 mL of hydrogel, 100 mg of other polymer material for adjusting physical properties, 2 mg of APS, 1 mg of TEMED, and liquid metal particles in which the surface of 400 μg was modified were included, thereby preparing the three-dimensional hydrogel composite of which physical properties were adjusted to enable finally injection.

The process of Examples 1 to 3 was schematized and shown in FIG. 1.

Experimental Example 1. Confirmation of the Temperature Increase Effect and Stability of Liquid Metal Particles with Surface Modification The effect of increasing the temperature of the surface-modified liquid metal particles prepared in Example 1 and the stability with the liquid metal particles of which the surface is not modified were confirmed as follows.

Figure 2:
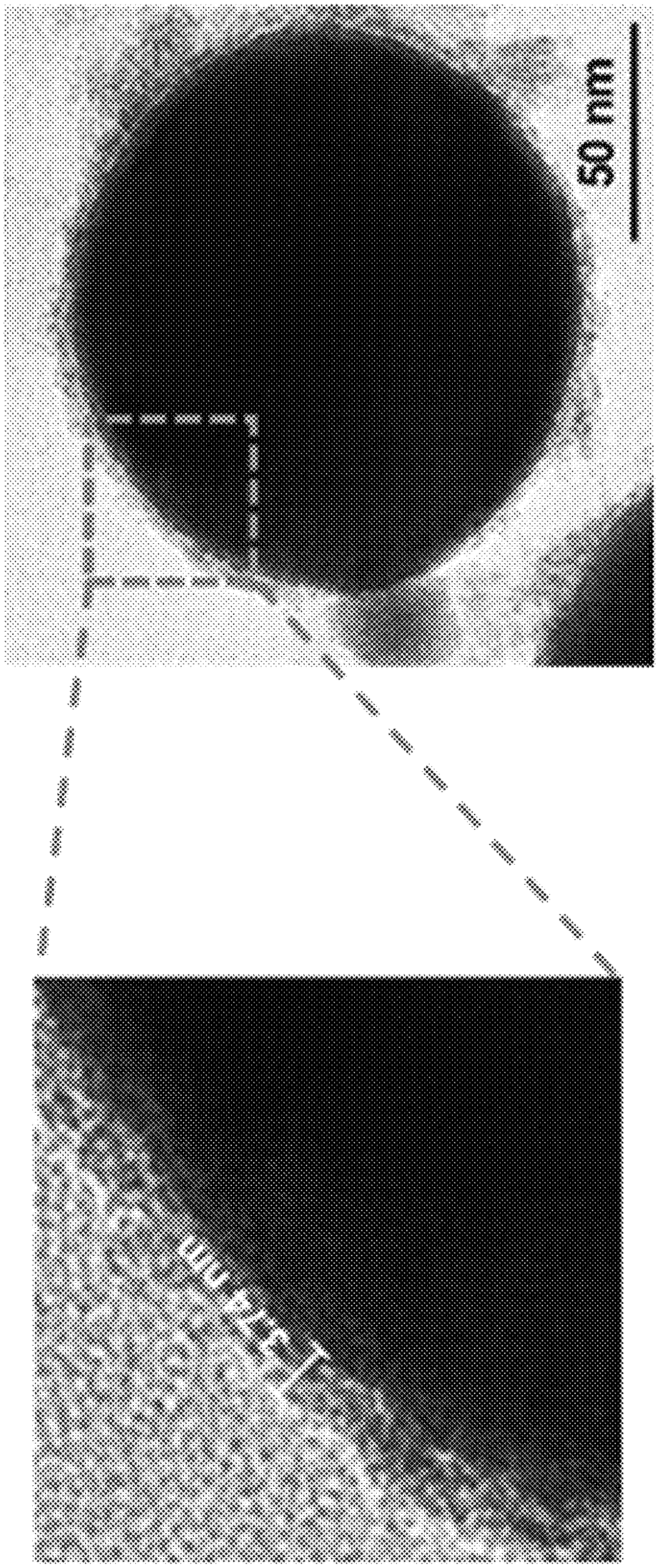
FIG. 2 is a diagram of the surface-modified liquid metal particles observed using transmission electron microscope.

First, as shown in FIG. 2, it was confirmed that the prepared surface-modified liquid metal had a spherical shape as a result of observation with a transmission electron microscope.

Thereafter, in order to confirm the effect of increasing the temperature when the near-infrared ray of the liquid metal particles having the modified surface prepared as described above is irradiated, a 200 μL liquid metal particle solution prepared by the process of Example 1 was prepared in a PCR tube and irradiated at a power density of 1.25 W/cm2 for 15 minutes using a near-infrared laser having a wavelength of 808 nm to confirm the effect of increasing the temperature.

Figure 3:
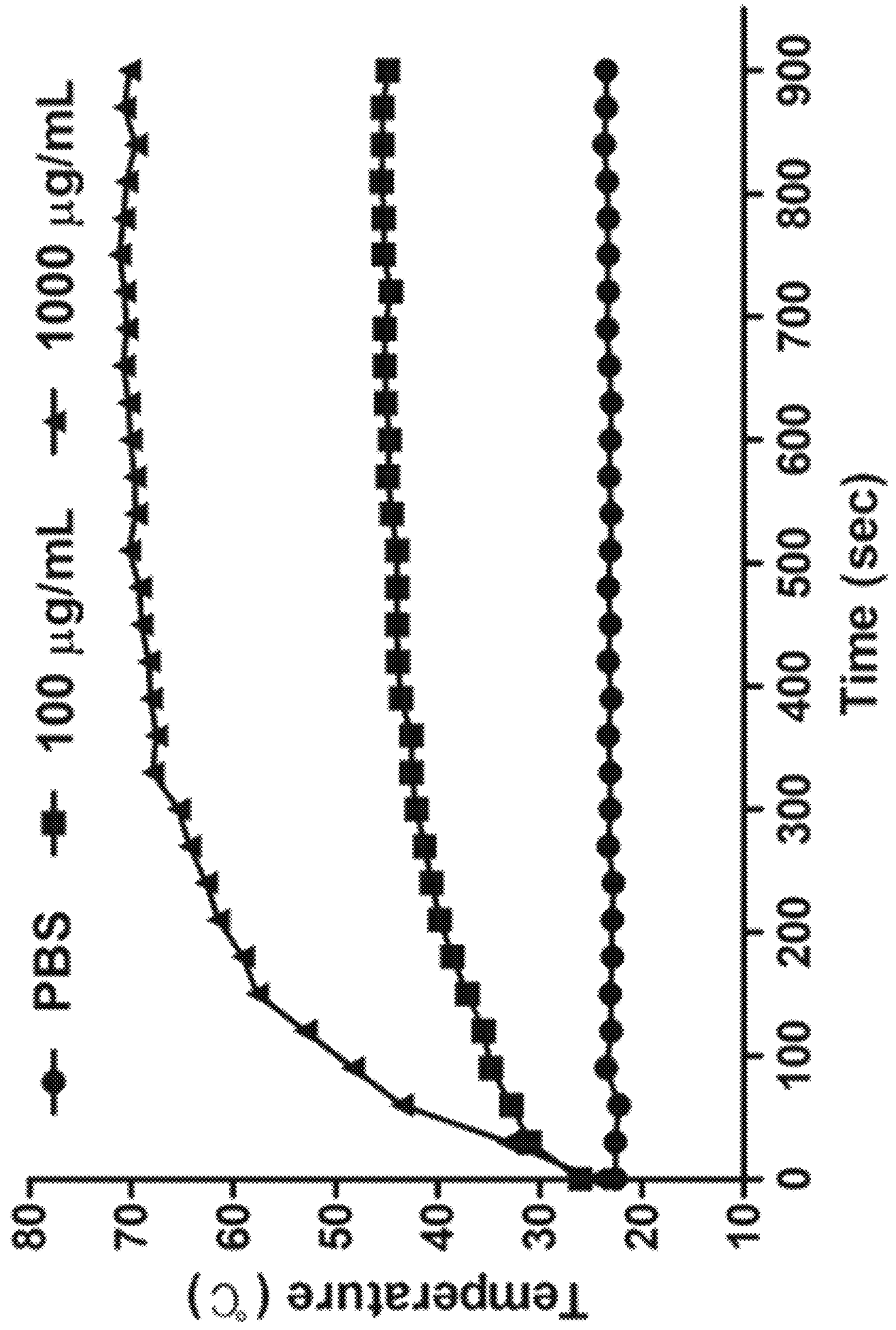
FIG. 3 is a diagram illustrating the effect of increasing the temperature after irradiating near-infrared rays to the surface-modified liquid metal particles.

As a result, as shown in FIG. 3, the surface-modified liquid metal of the present invention exhibits an increase in temperature upon near-infrared irradiation, and this temperature was temperature-dependently increased.

In addition, to confirm the stability of the surface-modified liquid metal particles, the absorbance spectrum was measured by collecting the supernatant at each specific time point using 2 mL of a liquid metal solution having a concentration of 2 mg/mL.

Figure 4:
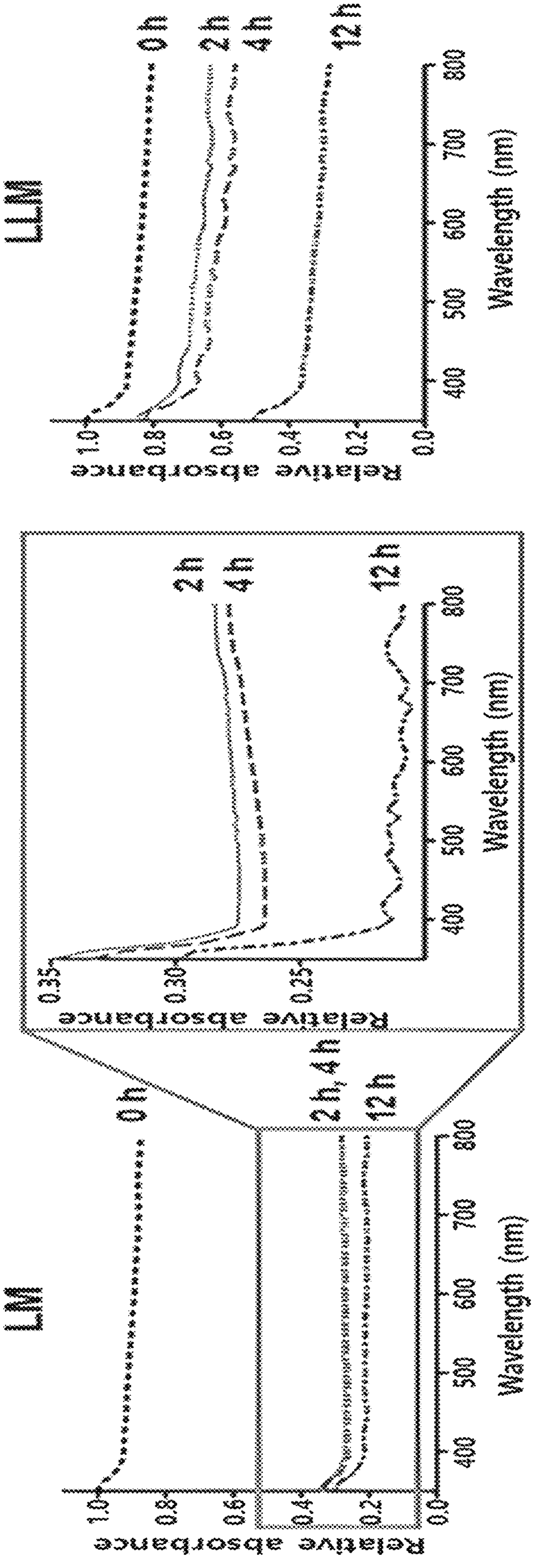
FIG. 4 is a diagram showing the degree of aggregation of surface-modified liquid metal particles and gallium-indium liquid metal particles without modification.

The results are shown in FIG. 4, and the surface-modified liquid metal with DSPE (1,2-Distearoyl-sn-glycero-3-phosphoethanolamine) are shown as LLM, and the surface-modified liquid metal with LM. As shown in FIG. 4, it was confirmed that the liquid metal particles (DSPE-EGaIn, LLM) of which the surface was modified using DSPE (1,2-Distearoyl-sn-glycero-3-phosphoethanolamine) had less aggregation in an aqueous solution and had stability during long-term storage compared to the liquid metal particles (EGaIn, LM) of which the surface was modified.

Experimental Example 2. Verification of Drug Release Using the Three-Dimensional Hydrogel In order to confirm the apoptotic effect of cancer cells resulting from the release of the anticancer agent due to the heat rise induced by near-infrared irradiation, the three-dimensional hydrogel was first manufactured according to the procedures outlined in Example 1 to 3. The three-dimensional hydrogel was prepared to have a diameter of 4.5 mm and a height of 1 mm. Subsequently, the drug released under different environmental conditions was examined.

Thereafter, the prepared three-dimensional hydrogel was placed in PBS or PBS containing 10 mM glutathione and stored at 100 RPM and 37° C. on a shaker table, and then used in a drug release experiment. In order to confirm the drug release, the liquid containing the three-dimensional hydrogel prepared as described above was collected on the day of 0 days (immediately after storage of glutathione) or 1, 2, 3, 4, 5, 8, 11, or 14 days after storage of glutathione, and was replaced with the same amount of PBS or PBS containing glutathione, and the released drug was quantified by measuring absorbance at 320 nm.

Figure 5:
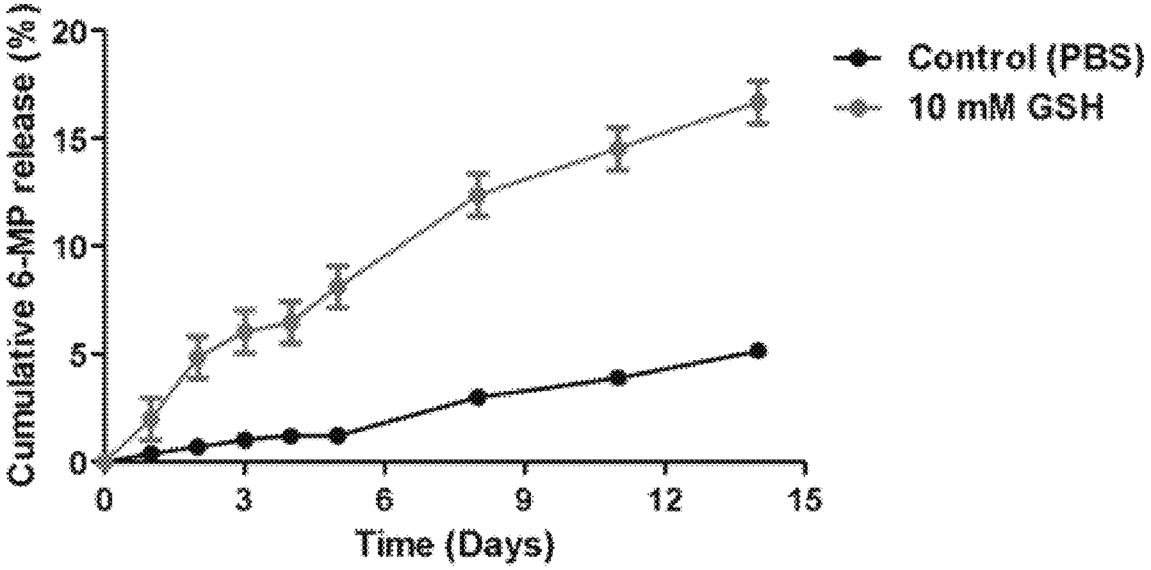
FIG. 5 is a diagram showing whether the three-dimensional hydrogel containing an anticancer drug releases the drug depending on environmental conditions.

As a result, as shown in FIG. 5, it was confirmed that the anticancer agent linked to the three-dimensional hydrogel of the present invention is connected to the polymer material through cleavable chemical bonds within the microenvironment of cancer cells/tissue. Therefore, drug can be released depending on reducing conditions of the cancer tissue microenvironment.

Experimental Example 3. Cytotoxicity Evaluation of the Three-Dimensional Hydrogel Composite The cytotoxicity evaluation of the three-dimensional hydrogel composites prepared through the same processes as in Examples 1 to 3 was performed.

MDA-MB-231 DMEM breast cancer cells were inoculated at a density of $4\times10^4$ cells per well on a 48-well plate prepared with 10% FBS and 1% penicillin/streptomycin and cultured at 37° C. for one day. Thereafter, the hydrogel of each group prepared to have a diameter of 4.5 mm and a height of 1 mm as in the above Example was treated, further incubated for 24 hours, washed with PBS, treated with a EZ-Cytox solution, incubated for 2 hours at 37° C., and cytotoxicity was evaluated through measurement of absorbance at 450 nm.

Figure 6:
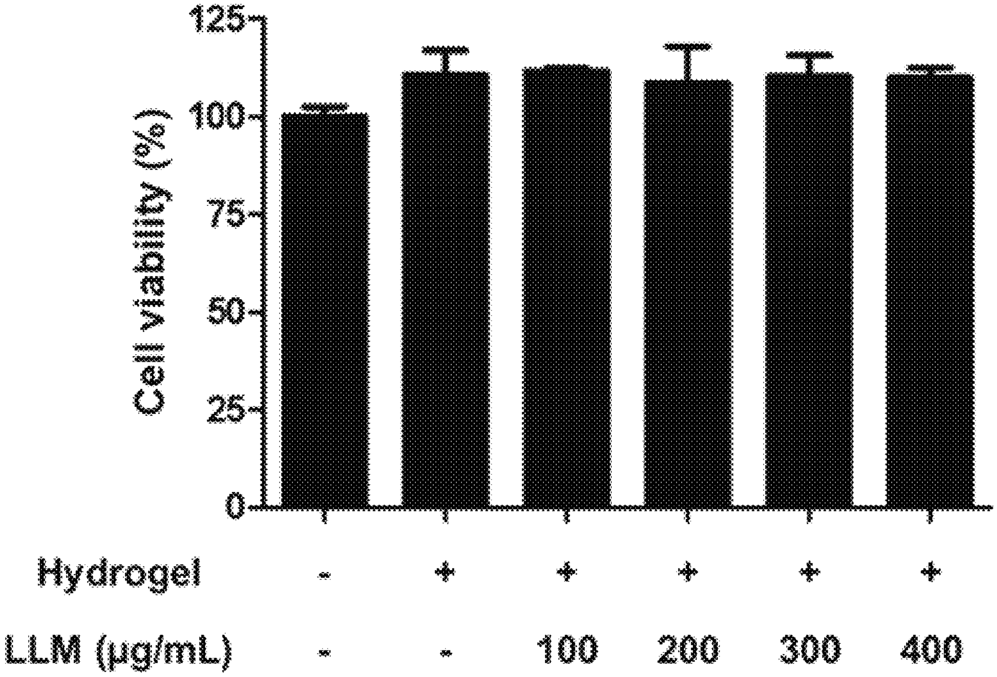
FIG. 6 is a diagram illustrating a result of evaluation of cytotoxicity of the three-dimensional hydrogel.

As a result, as shown in FIG. 6, it was confirmed that even when the content of the liquid metal particles (LLM) included in the three-dimensional hydrogel was 400 microgram/mL, cytotoxicity was not exhibited, therefore it was confirmed that the three-dimensional hydrogel including the liquid metal particles of the present invention did not exhibit cytotoxicity.

Experimental Example 4. The Confirmation of the Photothermal Effect of the Three-Dimensional Hydrogel Composite A photothermal therapy is a treatment method of cancer by absorbing energy from photons and partially using the absorbed energy in the form of heat, and is a treatment method of inducing cancer cell apoptosis by increasing a temperature when a multi-nano-sized agent is accumulated near a tumor. In order to confirm the photothermal effect of the three-dimensional hydrogel composites prepared through the processes of Examples 1 to 3, an experiment was conducted as following.

Specifically, in order to confirm the photothermal effect according to the near-infrared irradiation intensity of the three-dimensional hydrogel composite prepared in the present invention, the near-infrared irradiation intensities were 0.5 W/cm$^2$, 1.0 W/cm$^2$, and 1.5 W/cm$^2$, respectively, using the three-dimensional hydrogel composite prepared in the above Example, and the irradiation intensities were 1.5 W/cm$^2$ using the hydrogel without the liquid metal particles of the present invention as control.

Figure 8:
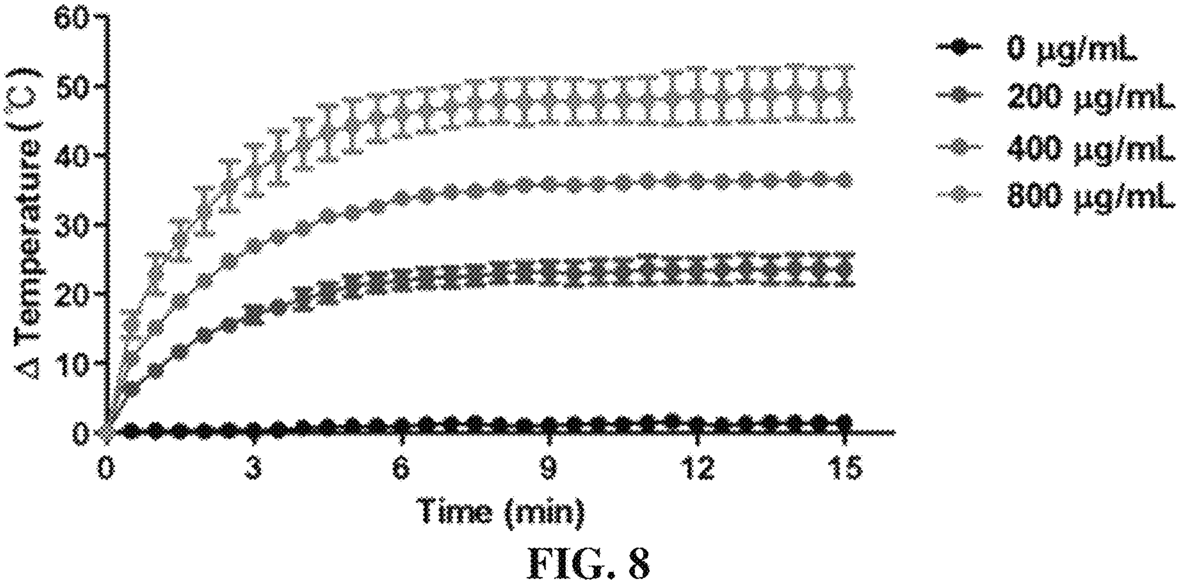
FIG. 8 is a diagram illustrating a comparison of temperature increase effects during near-infrared irradiation depending on concentration of liquid metal particles contained in the three-dimensional hydrogel.

In addition, in order to confirm the photothermal effect during near-infrared irradiation according to the concentration of the liquid metal particles contained in the three-dimensional hydrogel of the present invention, as shown in FIG. 8, the concentration of the liquid metal particles was 0 μg/ml, 200 μg/ml, 400 μg/ml, and 800 μg/ml, respectively, and the near-infrared irradiation condition was irradiated on 200 μL of hydrogel with intensity of 1.5 W/cm$^2$ and 808 nm laser for 15 minutes to record the temperature every 30 seconds.

Figure 7:
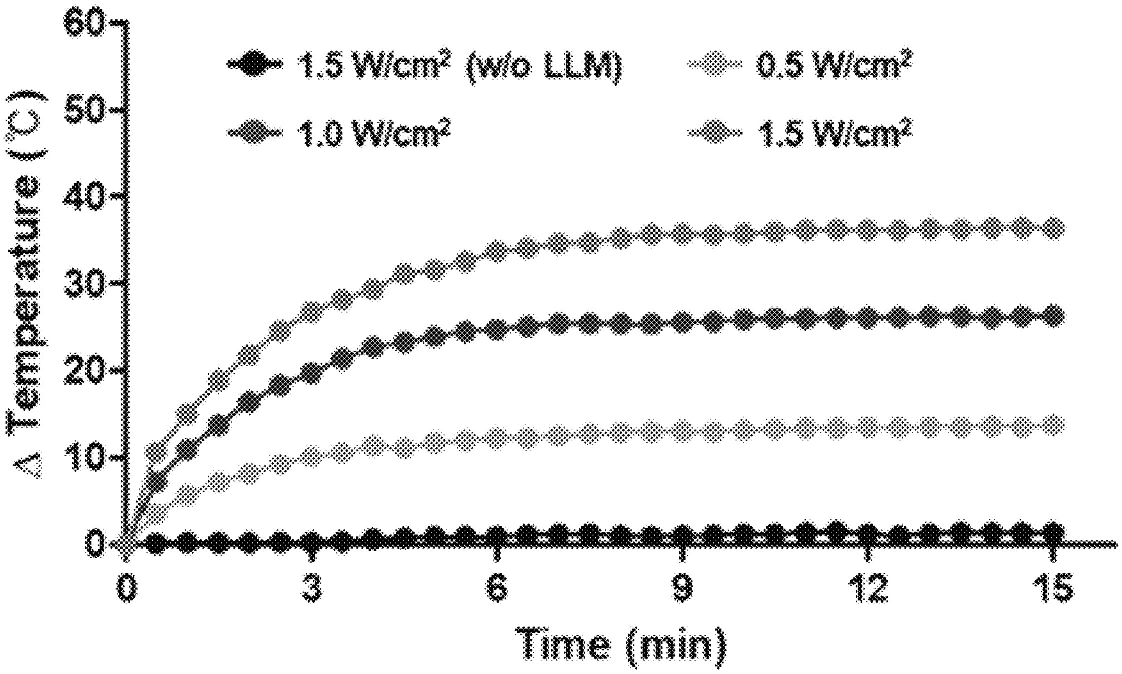
FIG. 7 is a diagram comparing and illustrating a temperature increasement effect depending on near-infrared intensity of the three-dimensional hydrogel.

As a result, as shown in FIG. 7, it was confirmed that even at the highest irradiation intensity of 1.5 W/cm$^2$ in the control group not including the liquid metal particles, the photothermal effect was insignificant and there was little change in temperature, but in the hydrogel composite including the liquid metal particles according to the Example, when the near-infrared irradiation intensity was increased to 0.5 W/cm2, 1.0 W/cm$^2$, and 1.5 W/cm$^2$, respectively, the temperature threshold over time showed a difference of 10~35° C. compared to the control group. That is, in the case of the control group, the photothermal effect was insufficient, but it was confirmed that the hydrogel composite containing the liquid metal particles of the present invention increased the photothermal effect according to the near-infrared irradiation intensity.

On the other hand, as shown in FIG. 8, the control group not including the liquid metal particles had little change in temperature due to a small photothermal effect, but in the hydrogel composite including the liquid metal particles according to the example, when the concentration of the liquid metal particles was increased, it was confirmed that the critical value of the temperature over time showed a difference of 20~45° C. compared to the control group. That is, it was confirmed that the photothermal effect also increased as the concentration of the liquid metal-based liquid increased.

Experimental Example 5-1. Confirmation of Temperature Elevation Effect and Generation of Reactive Oxygen Species for Cancer Cell Apoptosis by the Hydrogel Composite In order to confirm the apoptotic effect of the three-dimensional hydrogel composite manufactured through the same procedures as in Example 1 to 3, the following experiments were examined;

First, MDA-MB-231 breast cancer cell line and HCT-116 colon cancer cell line were inoculated on a 48-well plate at a density of 300 μL of 10% Fetal Bovine Serum (FBS), 1% penicillin/streptomycin-added Dulbecco's modified Eagle's medium (DMEM, Corning) per well, and $4\times10^4$ cells, and cultured in a cell incubator at 37° C. and atmospheric condition of 5% carbon dioxide for a day.

Thereafter, the cells were treated with a hydrogel containing 400 μg/mL of liquid metal and prepared to have a diameter of 4.5 mm and a height of 1 mm, and then irradiated with a laser having a wavelength of 808 nm at a strength of 1.5 W/cm$^2$ for 5 minutes and incubated at 37° C. for 48 hours.

After the culture, a EZ-Cytox cell viability assay reagent (WST-1 cell viability assay kit; DoGenBio, Seoul, Korea) was prepared to be 10% (v/v) per well.

For the WST-1 assay, the hydrogel was removed from the well plate, and then washed with 200 ul of PBS for each well, and 300 ul of EZ-Cytox cell viability assay reagent was added to the experimental group and the control wells.

The well plates were coated with foil and incubated for 2 hours at 37° C., after which 100 ul of the supernatant was transferred to a new 96-well plate and absorbance was measured at a wavelength of 450 nm using a microplate reader.

Figure 9A:
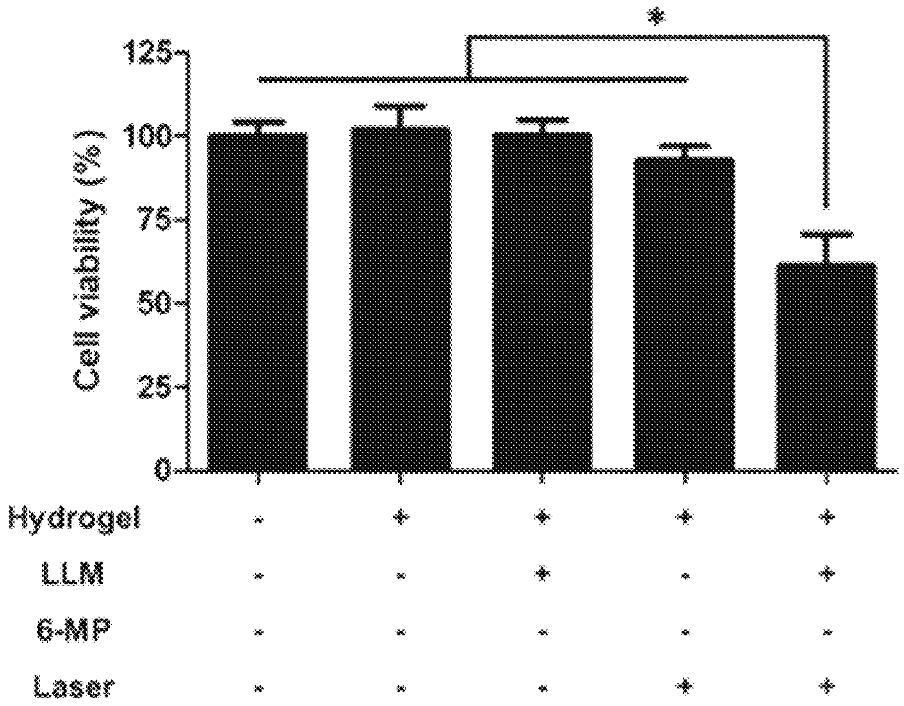
FIGS. 9A-9B are diagrams showing an effect of inducing cancer cell apoptosis of the three-dimensional hydrogel.

As depicted in FIG. 9A, the results indicate that when breast cancer cells without any treatment, treated with hydrogel alone, or treated with a hydrogel composite containing liquid metal particles, there was no significant apoptotic effect observed. Furthermore, when breast cancer cells were treated with hydrogel alone and irradiated with laser, the apoptotic effect was minimal. However, when breast cancer cells were treated with a hydrogel composite containing liquid metal particles and irradiated with laser, it was observed that 29-49% of breast cancer cells underwent apoptosis, compared to the negligible or absent apoptotic effect observed in the untreated or hydrogel-only treated groups.

Figure 9B:
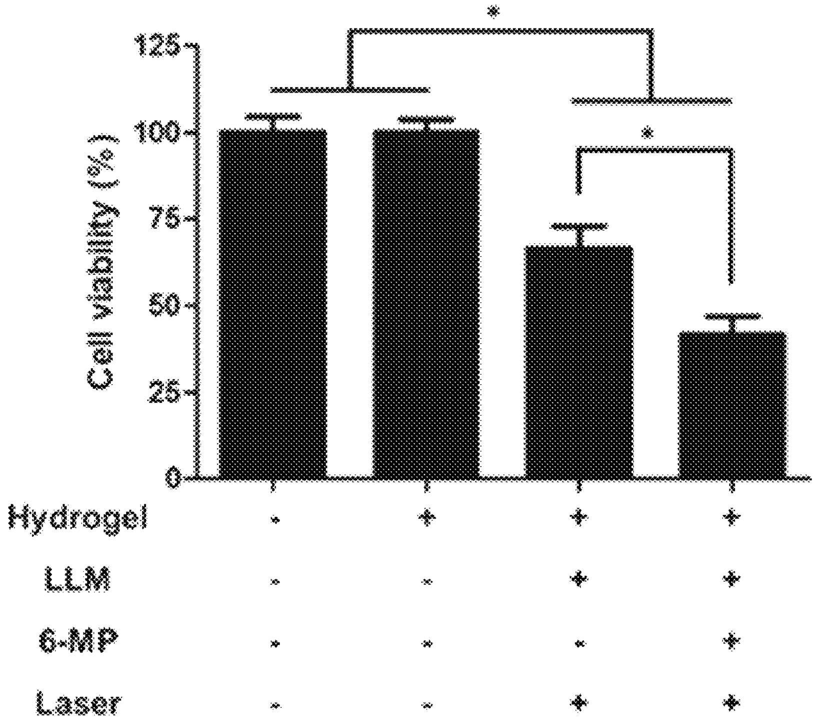

Meanwhile, as shown in FIG. 9B, when left untreated or treated with hydrogel alone, there was no apoptotic effect observed in colon cancer cells. However, when colon cancer cells were treated with a hydrogel composite containing liquid metal particles and irradiated with laser, 35% of the colon cancer cells underwent apoptosis, compared to the untreated group. Furthermore, when colon cancer cells were treated with a hydrogel composite containing both liquid metal particles and an anticancer agent linked to the hydrogel, and then irradiated with laser, it was observed that 60% of the colon cancer cells underwent apoptosis, compared to the untreated group.

That is, as illustrated in FIGS. 9A and 9B, it was confirmed that the photothermal effect of the hydrogel composite according to the near-infrared irradiation has a sufficient temperature increase effect to promote the induction of apoptosis of breast cancer cells.

In addition, in order to confirm the photo thermal effect in the pig skin (ex vivo porcine skin) similar to the human skin, a control group in which nothing was injected (control), a hydrogel containing no liquid metal particles and anti-cancer agent of the present invention, a hydrogel containing a liquid metal particle modified with a surface of 800 μg/mL (LLM-hydrogel), and a hydrogel containing both a liquid metal particle modified with a surface of 800 μg/mL and an anti-cancer agent (LLM-6MP@hydrogel) were injected into the pig skin using a syringe, and a laser with a wavelength of 808 nm was irradiated with an intensity of 1.5 W/cm$^2$ for 5 minutes to confirm the temperature rising effect.

Figure 10:
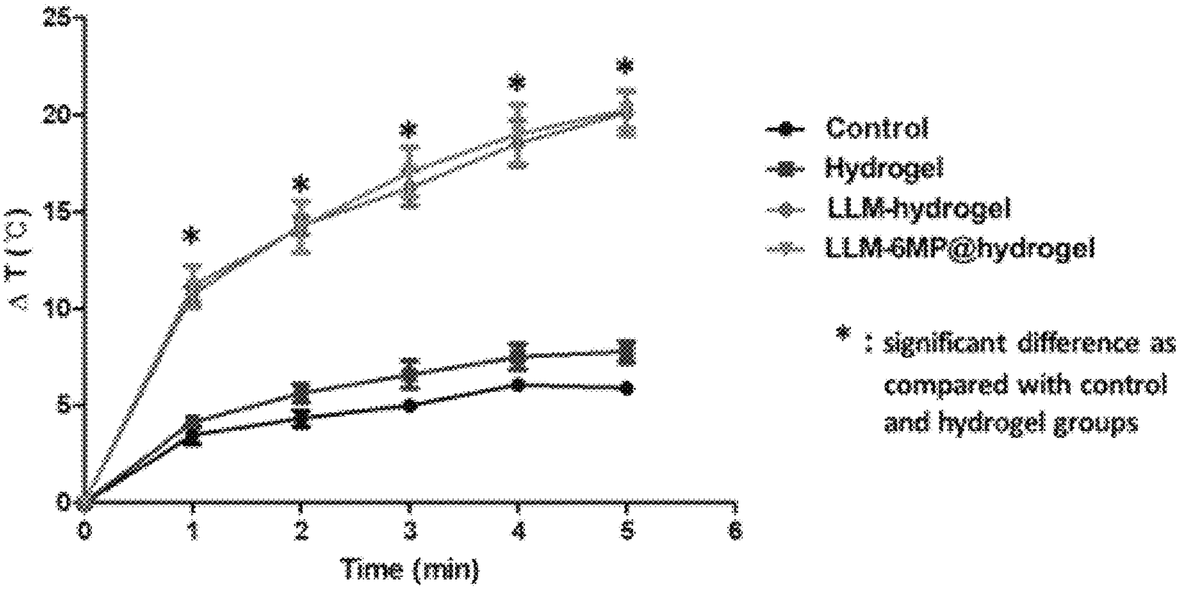
FIG. 10 is a diagram illustrating a temperature rising effect investigated when the 3-dimensional hydrogel with near-infrared irradiation for inducing apoptosis of cancer cells in the subcutaneous area using pig skin.

As a result, as shown in FIG. 10, when laser was irradiated onto the skin of a pig (ex vivo porcine skin) similar to the human skin, the threshold temperature of the pig was 6° C. when nothing was injected thereinto, and the threshold temperature of the pig was 8° C. when only hydrogel containing no liquid metal particles and no anticancer agent was injected thereinto.

Meanwhile, as shown in FIG. 10, when a hydrogel (LLM-hydrogel) containing liquid metal particles at a concentration of 800 μg/mL was injected into a porcine skin (ex vivo porcine skin) similar to human skin, and a hydrogel (LLM-6MP@hydrogel) containing liquid metal particles at the same time of 800 μg/mL and a 6-MP anticancer agent was injected into the porcine skin, the threshold of the temperature over time was 18° C.

When the hydrogel (LLM-hydrogel) containing the liquid metal particles at a concentration of 800 μg/mL was injected into the pig skin (ex vivo porcine skin) similar to the human skin, and when the hydrogel (LLM-6MP@hydrogel) containing the surface-modified liquid metal particles of 800 μg/mL and the 6-MP anticancer agent at the same time was injected thereto, a temperature difference between the temperature and the temperature was 12~14° C., compared to when nothing was injected into the pig skin (ex vivo porcine skin) similar to the human skin and when only the hydrogel containing no liquid metal particles and anticancer agent was injected thereto.

That is, when the near-infrared irradiation is performed on the injected hydrogel composite, it was confirmed that the hydrogel without the liquid metal and the anticancer agent of the control group and the present invention has an insignificant effect of increasing the temperature, but the hydrogel with a modified surface (LLM-hydrogel) and a liquid metal concentration of 800 μg/mL, and the hydrogel including the anticancer agent (LLM-6MP@hydrogel) has an excellent effect of increasing the temperature for inducing apoptosis of cancer cells in the subcutaneous area.

In addition, in order to confirm the effect of inducing apoptosis of cancer cells by active oxygen, DPBF was first dissolved in 30% ethanol and 70% water to prepare a concentration of 30 μg/mL, and then mixed with hydrogel in the dark for 2 hours. Then, the absorbance spectrum was measured by irradiating a laser with a wavelength of 808 nm with an intensity of 1.25 W/cm$^2$ for 10 minutes.

Figure 11:
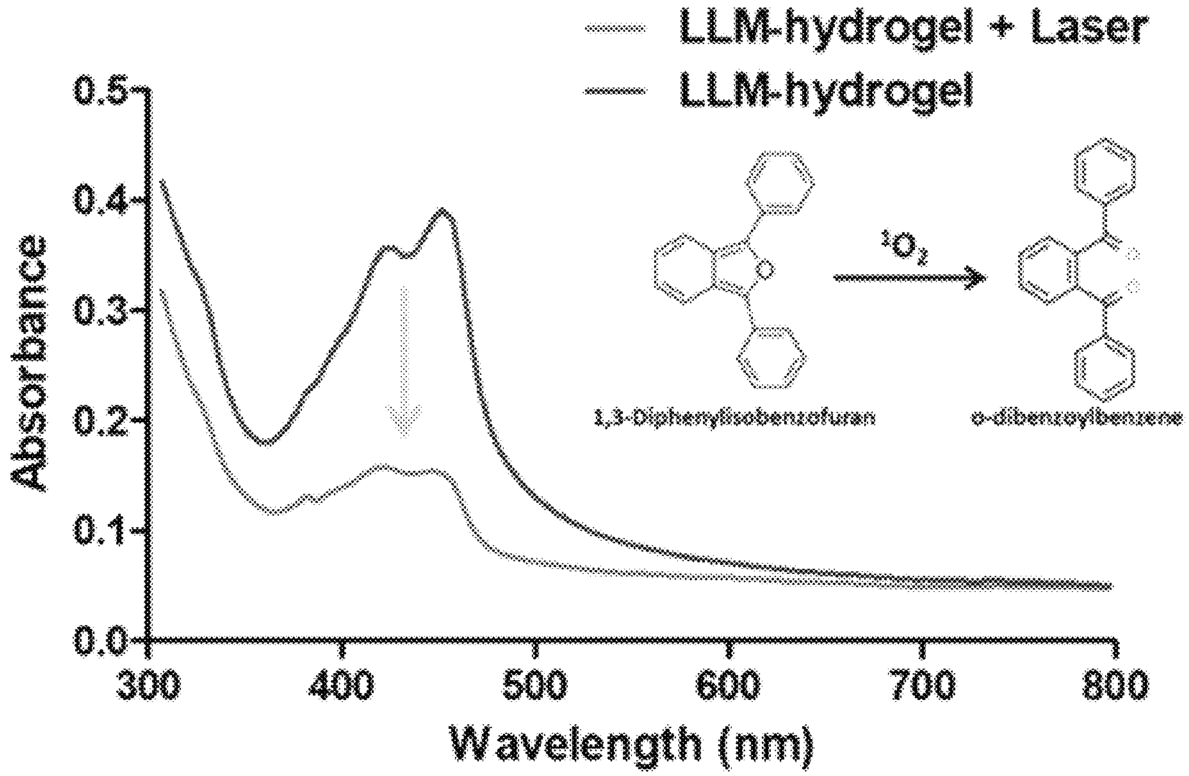
FIG. 11 is a diagram illustrating an effect of generating reactive oxygen species during near-infrared irradiation of the three-dimensional hydrogel.

As a result, as shown in FIG. 11, it was confirmed that the absorbance value at a wavelength of 450 nm was relatively reduced compared to the case where the laser was not irradiated, and through this, active oxygen was generated.

That is, it was confirmed that the liquid metal particles included in the hydrogel composite of the present invention have an effect of inducing additional cancer cell apoptosis by generating reactive oxygen by inducing a change in oxygen molecules present in the periphery of the administration site in response to near-infrared irradiation.

Experimental Example 5-2. Confirmation of a Temperature Rise Effect of a Hydrogel and an Increased Apoptosis of Cancer Cells Due to a Release of an Anticancer Agent In order to confirm the apoptotic effect of cancer cells of the three-dimensional hydrogel composite manufactured through the procedures outlined in Example 1 to 3, the following experiemtns were conducted;

First, HeLa cervical cancer cell line was inoculated on a 48-well plate at a density of 300 μl of 10% Fetal Bovine Serum (FBS) and 1% penicillin/streptomycin-added Dulbecco's modified Eagle's medium (DMEM, Corning) per well and $3\times10^4$ cells, and cultured in a cell incubator at 37° C. and 5% carbon dioxide for one day.

Thereafter, the cells were treated with a hydrogel containing 400 μg/mL of liquid metal and prepared to have a diameter of 4.5 mm and a height of 1 mm, and then irradiated with a laser having a wavelength of 808 nm at an intensity of 0.2 W/cm$^2$ for 5 minutes, and incubated at 37° C. for 48 hours.

After the culture, a EZ-Cytox cell viability assay reagent (WST-1 cell viability assay kit; DoGenBio, Seoul, Korea) was prepared to be 10% (v/v) per well.

For the WST-1 assay, the hydrogel was removed from the well plate, followed by washing with 200 ul of PBS per well, and 300 ul of EZ-Cytox cell viability assay reagent was added to the experimental group and the control wells.

The well plates were coated with foil and incubated for 2 hours at 37° C., after which 100 μl of the supernatant was transferred to a new 96-well plate and absorbance was measured at a wavelength of 450 nm using a microplate reader.

Figure 16:
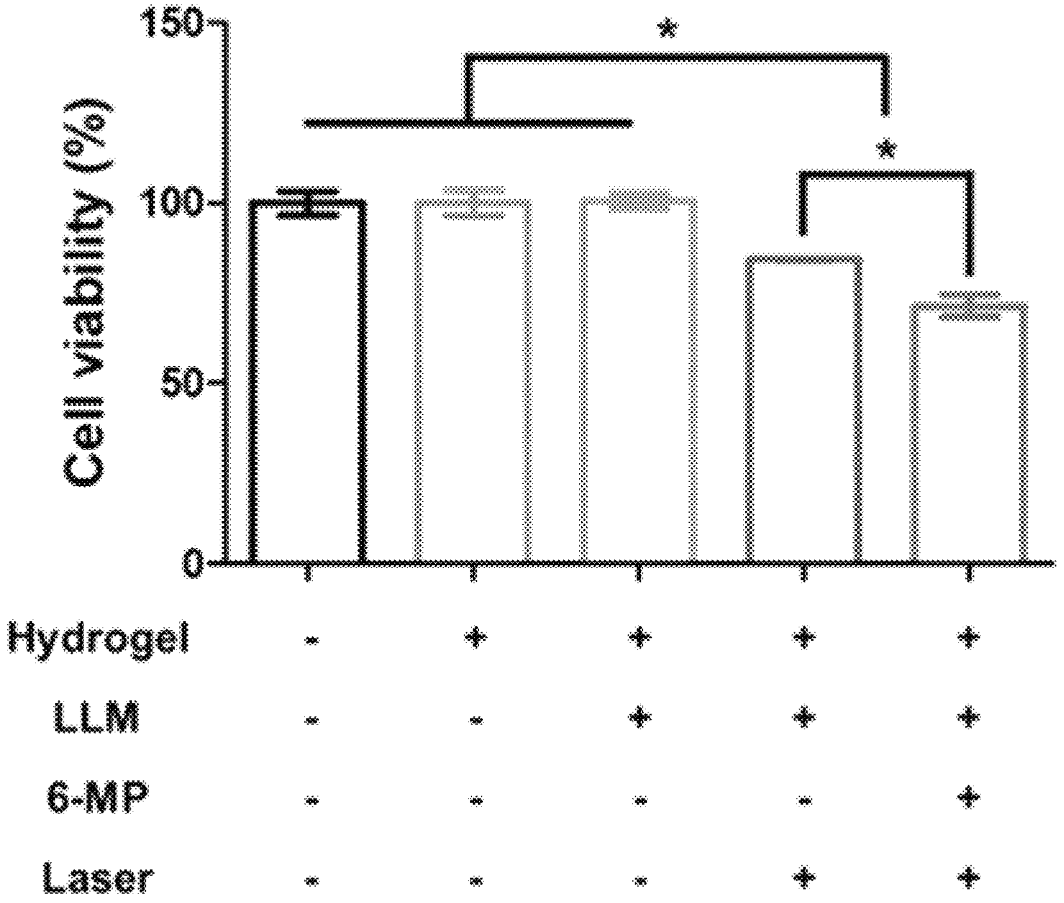
FIG. 16 is a diagram showing an improved cancer cell apoptosis-inducing effect of the three-dimensional hydrogel.

As a result, as shown in FIG. 16, when cervical cancer cells were not treated with any treatment, when cervical cancer cells were treated with hydrogel alone, and when cervical cancer cells were treated with a hydrogel composite containing liquid metal particles, there was no effect of killing cervical cancer cells. However, when cervical cancer cells were treated with a hydrogel composite containing liquid metal particles and irradiated by laser, 15% of cervical cancer cells died, compared to the case where there was no effect of apoptosis of cervical cancer cells. In addition, when cervical cancer cells were treated with a hydrogel composite containing liquid metal particles and connected to an anticancer agent and irradiated by laser, 30% of cervical cancer cells were killed compared to the case where there was no effect of apoptosis of cervical cancer.

That is, it was confirmed that the photothermal effect of the hydrogel composite according to the near-infrared irradiation has a sufficient temperature increase effect compared to the group not irradiated with the laser, and has an excellent effect of inducing apoptosis of cervical cancer cells by inducing the release of the anticancer agent contained in the hydrogel.

Experimental Example 6. Verification of the Apoptotic Effect of Anticancer Agents Released by Chemical Bond Cleavage in the Microenvironment of Cancer Tissue The three-dimensional hydrogel of the present invention induces apoptosis in cancer cells through a photothermal effect upon near-infrared irradiation. Subsequently, substances such as glutathione released from the apoptotic cancer cells enhance the reducting conditions of the microenvironment of cancer tissue, thereby promoting the cleavage of disulfide bonds connecting the hydrogel and the anticancer agent. This cleavage leads to the release of the anticancer agent, which further induces additional apoptosis of surrounding cancer cells, thereby enhancing the anticancer effect.

The apoptotic effect resulting from the release of anticancer agents was confirmed by comparing the effects of anticancer agents released due to chemical bond cleavage during photoirradiation with that of anticancer agents at the same concentration.

The three-dimensional hydrogels prepared according to Examples 1 to 3 to have a diameter of 8 mm and a height of 2 mm were stored together with 1 mL of PBS at 37° C. and 100 RPM. MDA-MB-231 breast cancer cells were inoculated at a density of $4\times10^4$ cells per well on a 48-well plate prepared with DMEM supplemented with 10% FBS and 1% penicillin/streptomycin and cultured at 37° C. for one day. After removal of the existing medium, cancer cells were treated with 50 μL of fresh medium and 150 μL of PBS containing released 6-MP, and incubated at 37° C. for 24 h. For the WST-1 assay, the cells were washed with PBS, treated with EZ-Cytox solution in each experimental group, incubated at 37° C. for 2 hours, and then measured by absorbance at 450 nm to confirm the cell apoptosis effect.

Figure 12:
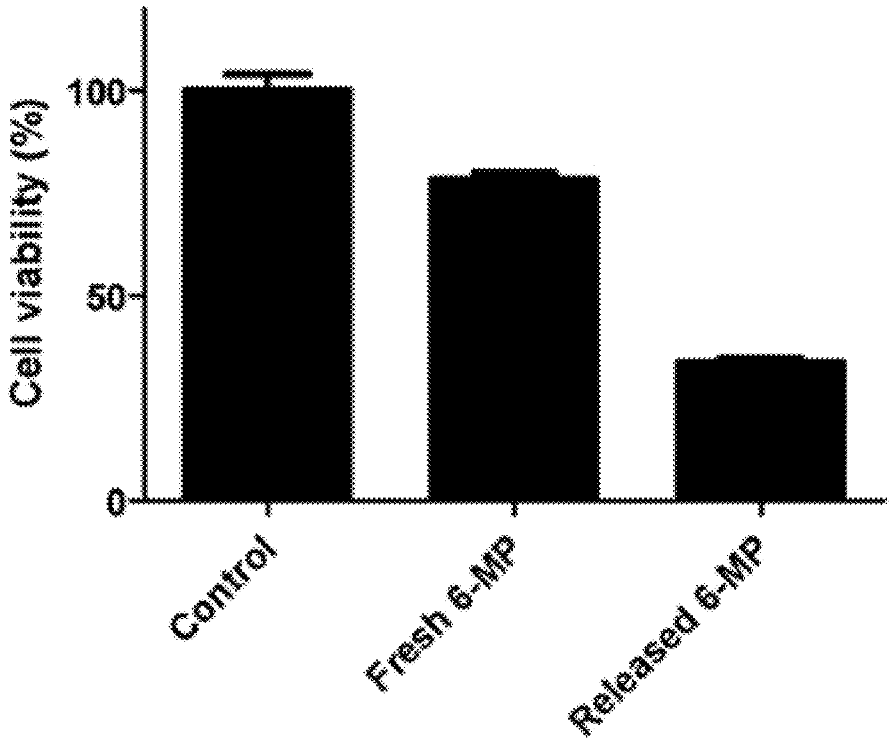
FIG. 12 is a diagram illustrating a comparison of the cancer cell killing effect of an anticancer drug released by the cleavage of chemical bond and the same anticancer drug under the simulated reducing condition of cancer tissue microenvironment.

As a result, as shown in FIG. 12, when breast cancer cells were not treated with any treatment, there was no effect of killing breast cancer cells. It was found that 21% of breast cancer cells died when treated with 6-MP not released by breast cancer cells, compared to the case where there was no effect of killing breast cancer cells. However, it was found that when treated with 6-MP released by cleavage of a chemical bond by a cell compound released from a dead cell during light irradiation, 70% of breast cancer cells were killed compared to the case where there was no effect of killing breast cancer cells.

Thus, it was confirmed that the apoptotic effect of anticancer agents released due to chemical bond cleavage under reducing conditions mimicking the microenvironment of cancer tissue was superior compared to the anticancer agents treated at the same concentration.

Experimental Example 7. A Confirmation of the Apoptotic Effect of the Hydrogel Composite Containing the Anticacner Agent In order to confirm the apoptotic effect of the three-dimensional hydrogel composite on cancer cells, the apoptotic effect was assessed as follows;

MDA-MB-231 breast cancer cells were inoculated at a density of $4\times10^4$ cells per well on a 48-well plate prepared with DMEM supplemented with 10% FBS and 1% penicillin/streptomycin and cultured at 37° C. for one day. Thereafter, each group of hydrogels prepared to contain liquid metal at a concentration of 400 μg/mL and have a diameter of 4.5 mm and a height of 1 mm were treated, and a laser with a wavelength of 808 nm was irradiated at an intensity of 0.2 W/cm2 for 5 minutes and incubated for 48 hours. After washing with PBS for the WST-1 assay, each experimental group was treated with a EZ-Cytox solution and incubated at 37° C. for 3 hours, and the cell apoptosis effect was confirmed by measuring absorbance at 450 nm.

Figure 13:
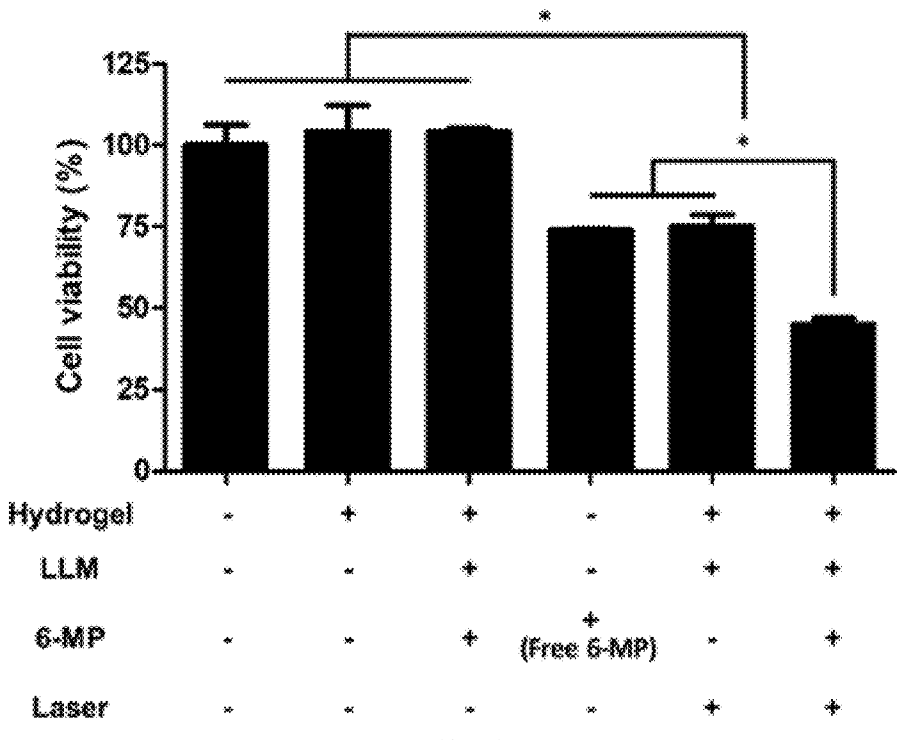
FIG. 13 is a diagram illustrating a cancer cell killing effect of the three-dimensional hydrogel containing an anticancer drug.

As a result, as shown in FIG. 13, when breast cancer cells were not treated with any treatment, when breast cancer cells were treated with hydrogel alone, and when breast cancer cells were treated with a hydrogel composite containing liquid metal particles and linked to an anticancer agent, there was no effect of killing breast cancer cells. However, when breast cancer cells were treated with a hydrogel composite containing liquid metal particles and irradiated by laser, 25% of the breast cancer cells were killed compared to the case where the breast cancer cell apoptosis effect was not effective or was insufficient. In addition, when breast cancer cells were treated with a hydrogel composite containing liquid metal particles and connected to an anticancer agent and irradiated by a laser, 55% of the breast cancer cells were killed compared to the case where the breast cancer cell killing effect was not effective or was insufficient.

That is, it was confirmed that when near infrared rays are irradiated on the three-dimensional hydrogel containing both liquid metal particles (LLM) and an anticancer agent (6-MP), cancer cell apoptosis effects are very excellent. Through this, it was confirmed that the hydrogel composite of the present invention induces cancer cell apoptosis more effectively than the photothermal effects of liquid metals or the respective cancer cell apoptosis effects of anticancer agents due to the subsequent release of anticancer agents and cancer cell apoptosis due to photothermal effects of liquid metals caused by an increase in the photothermal effect mediated temperature of liquid metals.

Experimental Example 8. Confirmation of a Temperature Control Effect According to Near-Infrared Irradiation The three-dimensional hydrogel composites prepared through the same procedures as in Examples 1 to 3 were tested as follows in order to confirm the temperature control effect according to the near-infrared irradiation and the thermal stability through the repetition of temperature rise and fall.

Hydrogel, hydrogel containing liquid metal particles (LLM-hydrogel), hydrogel containing anticancer agent (6MP@hydrogel), and hydrogel containing both liquid metal and anticancer agent (LLM-6MP@hydrogel) were each injected into PCR tubes at 200 μL. These were then subjected to near-infrared irradiation or non-irradiation using an 808 nm laser at an intensity of 1.5 $W/cm^2$ with a 6-minutes on/4-minutes off cycle repeated 5 times. The temperature was recorded every 30 seconds.

Figure 14:
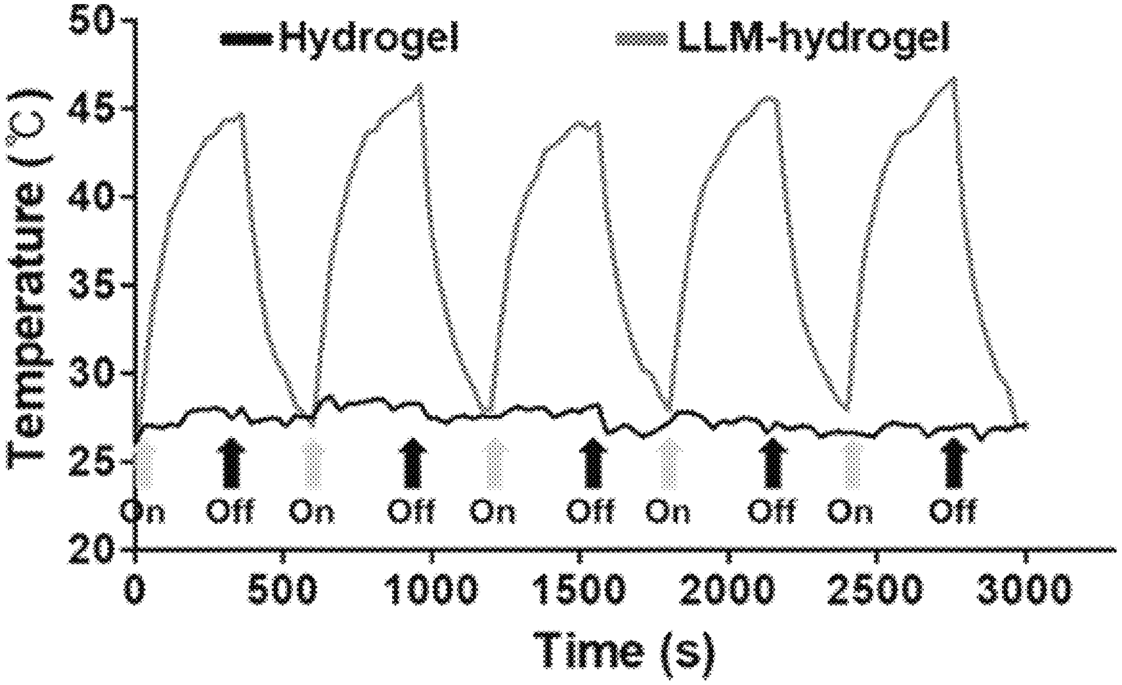
FIG. 14 is a diagram illustrating an effect of increasing or decreasing a temperature according to whether the three-dimensional hydrogel with near-infrared ray irradiation.

As a result, as shown in FIG. 14, when near-infrared rays were irradiated to the hydrogel (LLM-hydrogel) containing liquid metal particles, the temperature was increased, and when near-infrared rays were not irradiated, the temperature was decreased, and the temperature was repeatedly increased all five times.

Figure 15:
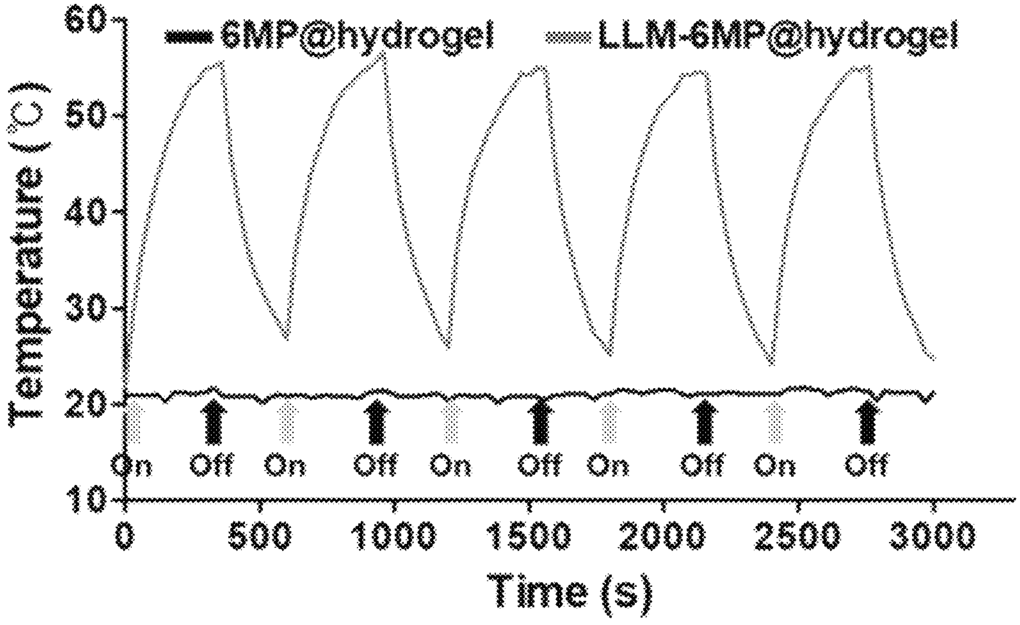
FIG. 15 is a diagram illustrating an effect of increasing or decreasing a temperature depending on whether the three-dimensional hydrogel containing an anticancer drug with near-infrared ray irradiation.

In addition, as shown in FIG. 15, even when near-infrared rays are irradiated or not irradiated to the hydrogel (LLM-6MP@hydrogel) containing both the liquid metal and the anticancer agent, it was confirmed that there was an effect of increasing the temperature when the near-infrared rays are irradiated, and there was an effect of decreasing the temperature when the near-infrared rays are not irradiated.

As shown in the above results, in the three-dimensional hydrogel composite, liquid metal particles are essential to increase the temperature due to near-infrared irradiation, and have an excellent cancer cell killing effect due to the release of anticancer agents during near-infrared irradiation, and thus it was confirmed that the three-dimensional hydrogel composite of the present invention has an excellent effect when used in combination of photothermal therapy and chemotherapy.

The above description of the present invention is for illustration, and those skilled in the art to which the present invention pertains will understand that the present invention can be easily modified into other specific forms without changing the technical idea or essential features of the present invention.

Therefore, it should be understood that the embodiments described above are exemplary in all aspects and are not restrictive. For example, each element described as a single type may be distributed and implemented, and similarly, elements described as being distributed may also be implemented in a combined form.

The scope of the present invention is represented by the following claims rather than the above detailed description, and it should be interpreted that the meaning and scope of Claims and all changes or modified forms derived from the equal concept thereof are included in the scope of the present invention.

INDUSTRIAL APPLICABILITY

According to the present invention, the three-dimensional hydrogel composite of the present invention comprises liquid metal particles which have a property of being injectable and have a cancer cell killing effect by causing a photothermal reaction by means of near infrared rays, and an anticancer agent which can be released into a cancer tissue, and thus can be used in a combination of photothermal therapy and chemotherapy. Therefore, the three-dimensional hydrogel composite of the present invention is an injection-type preparation of local cancer tissue, comprising gallium-indium liquid metal particles capable of inducing a photothermal effect for effective treatment of cancer diseases and an anticancer agent capable of inducing cancer cell apoptosis, and is thus widely industrially applicable for the treatment of various cancer cells.

The invention claimed is:

1. The three-dimensional hydrogel for photothermal therapy and chemical therapy, comprising liquid metal particles of which surfaces are modified and an anticancer agent immobilized by a chemical bond.

2. The three-dimensional hydrogel according to claim 1, wherein the anticancer agent is immobilized by a disulfide bond with a polymer material, and the polymer material is gelatin.

3. The three-dimensional hydrogel according to claim 1, wherein the surface-modified liquid metal particles are surface-modified with at least one selected from the group consisting of DSPC (1,2-distearoyl-sn-glycero-3-phosphocholine), DSPE (1,2-Distearoyl-sn-glycero-3-phosphoethanolamine), DOPE (1,2-Dioleoyl-sn-glycero-3-phosphoethanolamine), dextran and poly(ethylene glycol) (PEG).

4. The three-dimensional hydrogel according to claim 1, wherein the liquid metal particle is any one or more selected from the group consisting of gold, platinum, silver, and gallium-indium.

5. The three-dimensional hydrogel according to claim 1, wherein the anticancer agent is any one or more selected from the group consisting of 6-mercaptopurine, doxorubicin, 5-fluorouracil, paclitaxel, docetaxel, and gemcitabine.

6. The three-dimensional hydrogel according to claim 1, wherein the hydrogel further comprises poly(ethylene glycol) diacrylate, and thus its physical properties are adjusted to enable injection.

7. The three-dimensional hydrogel according to claim 1, wherein the hydrogel has the three-dimensional structure and induces cancer cell apoptosis due to a photothermal effect-mediated temperature rise of a liquid metal and subsequent release of an anticancer agent.

8. A preparation method of the three-dimensional hydrogel, the method comprising: (a) preparing liquid metal particles of which surfaces are modified; (b) fixing an anticancer agent by a chemical bond; and (c) mixing the liquid metal particles of which surfaces are modified in step (a) and the anticancer agent fixed by the chemical bond prepared in step (b) with other polymer materials to prepare the three-dimensional hydrogel composite of which physical properties are adjusted to enable injection.

9. The preparation method of the three-dimensional hydrogel according to claim 8, wherein the anticancer agent of step (b) is immobilized by disulfide bonding with a polymeric material, and the polymeric material is gelatin.

10. The preparation method of the three-dimensional hydrogel according to claim 8, wherein the other polymer material is poly(ethylene glycol) diacrylate.

11. The pharmaceutical composition for preventing or treating cancer according to claim 1, comprising the hydrogel.

12. The pharmaceutical composition for preventing or treating cancer according to claim 11, wherein the pharmaceutical composition for preventing or treating cancer induces the death of cancer cells due to the photothermal effect-mediated temperature increase of a liquid metal and subsequent release of an anticancer agent.

13. The pharmaceutical composition for preventing or treating cancer according to claim 11, wherein the cancer is solid tumor.

14. The pharmaceutical composition for preventing or treating cancer according to claim 13, wherein the solid tumor is any one or more selected from the group consisting of gastric cancer, liver cancer, glioblastoma, ovarian cancer, colorectal cancer, head and neck cancer, cervical cancer, bladder cancer, renal cell cancer, breast cancer, metastatic cancer, prostate cancer, pancreatic cancer, melanoma, esophageal cancer, colon cancer, hepatocellular cancer and lung cancer.

* * * * *